(12) United States Patent
Sonnenhol et al.

(10) Patent No.: US 7,605,384 B2
(45) Date of Patent: Oct. 20, 2009

(54) APPARATUS FOR AND METHOD OF PREPARING A SMALL AMOUNT OF A RADIOACTIVE SUBSTANCE COMBINATION

(75) Inventors: Julian Bernd Sonnenhol, München (DE); Andreas Eursch, Garnisch Partenkirchen (DE); Mark Harfensteller, Munchen (DE); Michael Schilp, Garching (DE); Oliver Buck, Bayerisch Gmain (DE); Lisa Maria Ehrenfried, Erlenbach (DE); Tuomo Nikula, Ottobrunn (DE)

(73) Assignee: Isotopen Technologien Munchen AG (DE)

( * ) Notice: Subject to any disclaimer, the term of this patent is extended or adjusted under 35 U.S.C. 154(b) by 150 days.

(21) Appl. No.: 11/816,152

(22) PCT Filed: May 11, 2006

(86) PCT No.: PCT/EP2006/004438

§ 371 (c)(1),
(2), (4) Date: Dec. 17, 2007

(87) PCT Pub. No.: WO2007/006359

PCT Pub. Date: Jan. 18, 2007

(65) Prior Publication Data

US 2008/0224072 A1   Sep. 18, 2008

(30) Foreign Application Priority Data

Jul. 7, 2005   (DE) .................. 10 2005 031 920

(51) Int. Cl.
*G21F 5/02* (2006.01)

(52) U.S. Cl. ............... 250/496.1; 250/432 PD; 250/432 R; 250/430; 250/336.1; 250/336; 250/364; 422/71; 422/159; 141/9; 141/27; 141/104; 252/625

(58) Field of Classification Search .......... 250/496.1, 250/432 PD, 432 R, 430, 336.1, 336, 364; 422/71, 159; 141/9, 27, 104; 252/625
See application file for complete search history.

(56) References Cited

U.S. PATENT DOCUMENTS

| | | | | |
|---|---|---|---|---|
| 4,409,488 A | * | 10/1983 | King ................. | 250/432 PD |
| 4,625,118 A | * | 11/1986 | Kriwetz et al. ....... | 250/432 PD |
| 4,853,546 A | * | 8/1989 | Abe et al. ........... | 250/432 PD |
| 5,039,863 A | * | 8/1991 | Matsuno et al. ...... | 250/432 PD |
| 5,674,742 A |   | 10/1997 | Allen et al. | |
| 6,157,036 A | * | 12/2000 | Whiting et al. ...... | 250/432 PD |
| 7,163,031 B2 | * | 1/2007 | Graves et al. ........ | 141/9 |
| 2004/0028573 A1 | | 2/2004 | Schmitz et al. | |

(Continued)

FOREIGN PATENT DOCUMENTS

CH           1420788           1/1976

(Continued)

*Primary Examiner*—Jack I Berman
*Assistant Examiner*—Meenakshi S Sahu PhD
(74) *Attorney, Agent, or Firm*—Saliwanchik, Lloyd & Saliwanchik

(57) ABSTRACT

The invention relates to an apparatus for preparing a small amount of a radioactive substance combination, including a one-part body, a mixing device integrated in the body and adapted to receive a small amount of chemical substances, and at least one receptacle integrated in the body and connected to the mixing device and adapted to hold a small amount of a chemical substance.

35 Claims, 1 Drawing Sheet

U.S. PATENT DOCUMENTS

2004/0197264 A1  10/2004  Schwarz et al.
2005/0002860 A1   1/2005  Filler et al.

FOREIGN PATENT DOCUMENTS

| DD | 271250 A3 | 8/1989 |
| DE | 19848312 C1 | 4/2000 |
| WO | WO 98/22625 A1 | 5/1998 |
| WO | WO 2004/093652 A2 | 11/2004 |

* cited by examiner

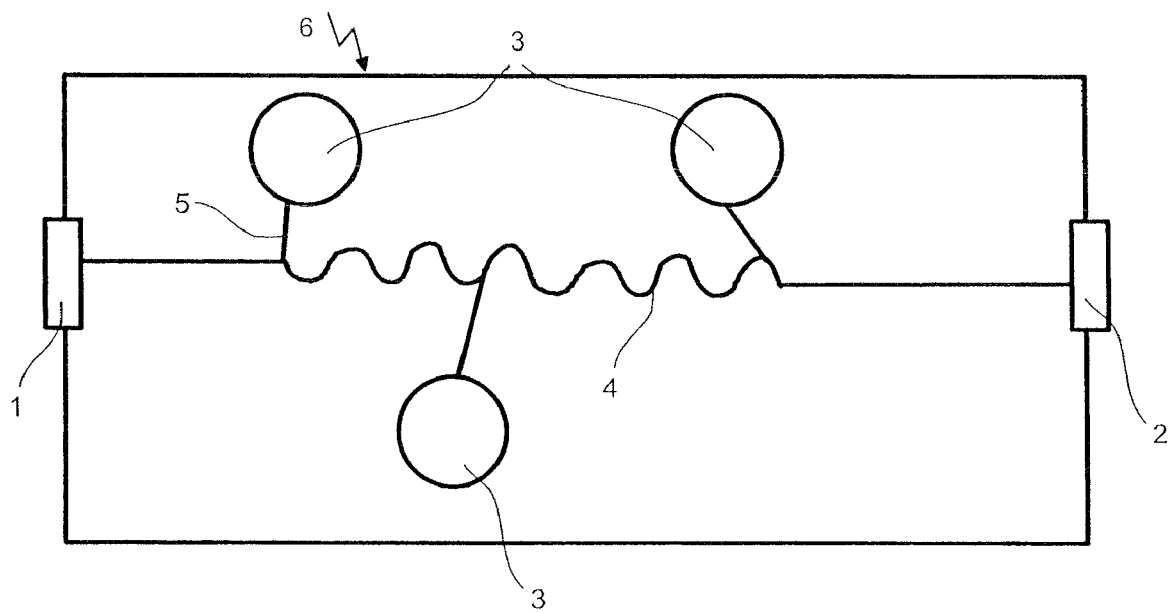

APPARATUS FOR AND METHOD OF PREPARING A SMALL AMOUNT OF A RADIOACTIVE SUBSTANCE COMBINATION

CROSS-REFERENCE TO RELATED APPLICATION

This application is the U.S. National Stage Application of International Patent Application No. PCT/EP2006/004438, filed May 11, 2006, the disclosure of which is hereby incorporated by reference herein in its entirety, including any figures, tables, or drawings.

The instant invention relates to an apparatus for preparing small quantities of a radioactive substance combination, especially small quantities of radiolabeled biomolecules, it also relates to a corresponding method of preparing the same.

In hospitals, radioactive isotopes are employed both in therapeutic and diagnostic applications.

The radioactive radiation emanating from isotopes is utilized for treating cancer, for pain therapy, and for wound dressing. To that end radioactive isotopes are introduced in various ways into the body. Possibilities to do so are binding them to organic metabolic agents, such as sugar or antibodies, injecting them into orifices of the body, introducing them in an enclosed, nonorganic envelope, such as a needle, capsule, or catheter. The isotopes chosen have adequate half-lifes and convenient types of radiation and, above all, their radius of radiation is as small as possible.

When applied for diagnostic purposes, radioactive isotopes used in imaging procedures allow metabolic processes to be made visible and individual cell species to be specifically localized. For this purpose, the isotopes are incorporated in molecules which take part in the metabolism, or they are coupled to suitable proteins, like monoclonal antibodies. Small dosage rates and a very short half-life of a few days, hours, and minutes, respectively, are aimed at so that a patient will suffer the least possible exposure.

It is a requirement to the production of medicines labeled with radioactive isotopes that chemical-physical processes must be carried out under controlled conditions. The decay characteristics of isotopes make it necessary to prepare such medicines in the vicinity of the place where they will be administered, for example in a hospital. At the present time, the preparation of such medicines in hospitals often involves many plug-in tubing connections to be made and a lot of individual components. Many times, such a structure can be used but once for making a single drug dose dedicated individually for just one patient. Adaptation and restructuring, respectively, are needed for every change in the preparation procedure, for instance to prepare another medicine for another patient. That requires manual interventions which may be accompanied by radioactive exposure of the operating staff. Persons may become contaminated also when handling substances during the preparation process.

Furthermore, whenever a medicine is prepared many individual components, such as hoses and vessels must be sterilized and cleaned before and after the preparation, respectively, whereby the cost of production of the medicine rises. Also, the disposal of some individual components may prove to be necessary, another factor adding to the costs.

In many cases no more than minute quantities of less than 10 ml are needed of a certain medicine containing radioactive isotopes and of correspondingly small amounts of starting substances. Manual handling and precise dosing of such very small quantities often is difficult to accomplish. As a rule, therefore, greater amounts of a certain medicine are prepared which are easier to handle but exceed the quantity needed for administration to a patient. Due to the individualized preparation, however, the remainder which was not administered cannot be used otherwise in most cases, but instead must be disposed of. Another cost increasing factor.

Manual preparation as practiced at present Is disadvantageous also because of inaccuracies in metering, particularly of small amounts.

It is, therefore, the object of the instant invention to provide an apparatus and a corresponding method permitting widely automatic preparation, individualized per patient, of a small amount, as required, of a radioactive substance combination and especially of biomolecules radiolabeled with isotopes.

This object is met by an apparatus as claimed in claim 1 and a corresponding method as claimed in claim 21.

Preferred embodiments of the invention are specified in the subclaims.

According to the invention, an apparatus is provided for preparing a small amount of a radioactive substance combination, including a one-part body, a mixing device integrated in the body and adapted to receive a small amount of chemical substances, and at least one receptacle integrated in the body and connected to the mixing device and adapted to hold a small amount of a chemical substance.

The apparatus according to the invention essentially is a miniaturized compact radiopharmaceutical production plant which can be operated substantially automatically and thus without, or almost without, human intervention. Small volumes of a radiochemical substance combination with precise mixing ratios can be prepared substantially automatically by this apparatus. The integrated structure, including at least one receptacle for holding a small quantity of a substance as well as a mixing device of corresponding dimensions connected to the receptacle, obviates the need for manually linking individual components. The apparatus preferably is a disposable item so that there is no need to clean it and, therefore, time, cleanser, and consequently expenses can be saved. The miniaturized design and size of the apparatus adapted to individualized single doses permit optimum utilization of the quantity of chemical substances used in the preparation. Only minor losses of substances occur due, e.g. to wetting of the walls of the apparatus, moreover, dead volumes can be widely avoided, and the residual amount remaining in the apparatus of any starting substances and radioactive substance combinations made can be minimized. The apparatus can be manufactured in great numbers at low cost, with the possibility of varying the structure of the apparatus, depending on the respective purpose for which it will be used.

The apparatus is adapted for mixing non-radioactive substances, like biomolecules, with radioactive isotopes. The radioactive isotopes are introduced into the apparatus in the vicinity of a corresponding reactor and an isotope source, respectively, which may be located in a hospital. Introduction into the apparatus, in particular into the mixing device integrated in the same, preferably is effected through an access which can be closed, e.g. a membrane or a mechanical lock. The non-radioactive substances, such as biomolecules or buffer solutions may be contained already in the one or more receptacles which are integrated in the apparatus. Or they may be fed into the apparatus together with one or more radioactive substances.

The apparatus may comprise one or more receptacles integrated in the apparatus and having a volume of less than 1 ml, preferably less than 100 µl, especially preferred being less than 10 µl. In this way those starting substances required for an individualized medicinal quantity which have a sufficiently long shelf life may be stored already in the apparatus in the specific amount needed. The combination of the chemical substances with one or more radioactive substances takes place inside the apparatus, particularly in the mixing device. At precise dosing, the minutest quantities are miscible almost perfectly within the shortest possible time, for example, within a few milliseconds. In comparison with systems designed for mixing greater amounts of substances, therefore, the binding degree and yield can be improved and a reduction of the process time achieved.

The apparatus especially may comprise one or more conduits integrated in the apparatus and having a volume of less than 5 ml, preferably less 100 µl, especially preferred being less than 10 µl. The apparatus thus preferably includes conduits adequate for the minutest quantities of chemical substances, whereby short connections can be assured to allow quick and essentially loss-free mixing of the substances. Considering their preferred small dimensions, only a small amount of manufacturing material is needed to make the apparatus on the whole, whereby manufacturing costs can be lowered.

The conduits preferably have a height of less than 500 µm, preferred being less than 100 µm and especially preferred less than 25 µm, and a width of less than 5 mm, preferred being less than 500 µm and especially preferred less than 100 µm. Due to the small cross sectional area of the conduits phenomena occurring in connection with liquids, such as capillary action, diffusion effects, Brown's molecular movement etc. are particularly pronounced and can be exploited for conveying and mixing mechanisms.

The conduits, in the first place serve as connections between the mixing device and one or more receptacles provided in the apparatus. However, they may function also as links between individual receptacles. According to a specific embodiment, the mixing device itself may be embodied by a conduit. Mixing in that case takes place by supplying two liquid substances to be mixed from one end of the conduit each, whereupon the substances become mixed as they meet, the mixing process being enhanced and accelerated by the microfluidic effects described above.

According to a preferred embodiment, the mixing device is selected from the group including cascade mixers, diffusion mixers, lamination mixers, mixers operating according to the split-recombine principle, mixers operating with the assistance of alternating electrical fields or with sonic or vibratory support. These mixers are especially well suited for mixing the minutest quantities of substances, and they operate while exploiting physical phenomena which occur to a significant degree with small liquid quantities and are known to persons skilled in the art. These are, for example, capillary action, Brown's molecular movement, etc.

The mixing device in particular has a capacity to hold less than 1 ml, preferably less than 100 µl, particularly preferred being less than 10 µl. Thus the desired radiochemical substance combination can be prepared in an amount adapted to a single dose for administration. Hereby the need of having to get rid of excess amounts can be avoided.

Moreover, the apparatus according to a preferred embodiment is closed and sealed, respectively, towards the outside. Thus chemical substances can be prevented from exiting the apparatus and contamination of persons is avoided. Contamination of the substances stored in the apparatus can be excluded as well. The sealing effect towards the outside, in the first place, is achieved by the integrated structure of the apparatus itself. Beyond that, it is possible to provide facilities for access which are adapted to be closed or sealed, like membranes or mechanical locks.

According to another embodiment, the apparatus includes at least one access, especially for a sensor, and/or a mechanical interface with the outside. Thanks to the access, sensor or measuring devices to carry out quality control can be inserted. Also chemical substances and especially radioactive isotopes may be supplied from outside into the mixing device through one or more mechanical interfaces, such as membranes or locks.

According to another embodiment, the apparatus includes at least one conveying and dosing means, respectively, of the group including means or a part of means operating with the use of centrifugal force, electrical force acting on a fluid, pressure or volume variation, or a conveying method functioning with sonic or vibratory support. The use of conveying and dosing means, respectively, which permit the respective dosing precision make it possible to supply accurate quantities of a chemical substance into the mixing device.

Furthermore, the apparatus may include at least one measuring or sensor means, especially for determining a physical magnitude from among the group including the type and power of radioactive radiation, pH, temperature, a means for carrying out chromatography or electrophoresis, and/or a means for detecting refraction of light and/or detecting at least one property of a substance from among the group including the presence or absence, quantity, color, and index of refraction, an ion exchange column, a size exclusion column or part thereof. The provision of one or several of these features can warrant quality assurance of the radioactive substance combination made. And the starting substances, too, which are either supplied to the apparatus or already contained inside can be verified as to their quality and quantity on the basis of suitable chemical or physical parameters.

For cost reasons, the measuring and sensor means preferably are provided partly inside the apparatus or integrated into the same, while electronic and mechanical components of these means for repeated use in connection with a plurality of apparatus preferably are located externally of the apparatus. The degree of automation of the preparation process can be further enhanced by the measuring or sensor means.

For automation of the preparation process, the apparatus according to another embodiment preferably is controllable from outside, including means for identification of the type of apparatus and means for receiving control and/or power supply signals for any possibly provided conveying and dosing means, respectively, measuring or sensor means, means for carrying out chromatography or electrophoresis, means for detecting refraction of light, for detecting properties of a substance, such as its presence, quantity, color, index of refraction, etc., for an ion exchange column or a size exclusion column. The means for receiving control and/or power supply signals may be embodied, for example, by leads provided directly on the apparatus on which they are formed especially by evaporation or sputter techniques. Or they may be transceiver means, inductive energy transfer means, remote control means operating on the basis of infrared or radio frequency signals, etc.

According to another preferred embodiment at least parts of the apparatus are manufactured as a monolith, especially by micro process engineering, including micro injection molding and micro embossing technology. In this manner, parts of the apparatus can be manufactured in great numbers at low cost. Conventional techniques, such as welding or bonding may be applied to connect the parts obtained by micro processing technology so as to complete the individual apparatus. Micro process engineering is well suited for precise shaping of the small conduits, receptacles, and mixing devices and the respective spaces to receive them in the apparatus. The monolithic structure contributes inherently to the external sealing of the apparatus since all the elements of the apparatus can be positioned or formed inside the same. Once finished, the apparatus is closed toward the outside, apart from access means which can be closed. Substances, therefore, cannot exit the apparatus so that the risk of contamination of persons can be avoided.

At the inside, the apparatus preferably includes coated surfaces to prevent substances from adhering or to catalyze chemical reactions. The apparatus also may include a heating and/or cooling means, or at least a part thereof, such as a heater wire or a Peltier element for acceleration and influencing, respectively, of the mixing processes or reactions. The apparatus preferably is made of plastics, especially of polyethylene, polypropylene, PMMA, PC, PTFE, COC (cycloolefin-copolymer), silicon, metal, or glass, or a combination thereof.

Moreover, the apparatus may be integrated in a system which includes a control unit adapted to be coupled to the apparatus. That offers a high degree of automation in producing doses of medicines individualized for each patient. The processes of preparation are reproducible and likewise may readily be individualized and varied, respectively. It is preferred to use each apparatus only once, with the possibility of coupling it to a repeatedly usable control unit.

Preferably, the system further includes an isotope source which can be coupled to the apparatus.

Finally, the system may include a conveying and dosing means, respectively, measuring or sensor means, a means for carrying out chromatography or electrophoresis, and/or a means for detecting refraction of light and/or detecting at least one property of a substance from among the group including the presence or absence, quantity, color, and index of refraction, an ion exchange column, a size exclusion column or part thereof, a sensor device for radioactivity, such as a scintillation counter, or part thereof.

Costs can be reduced by arranging these means externally of the apparatus because, being employed preferably for quality assurance, these means are useful with a great many apparatus for preparing individual doses of medicine.

According to the invention, moreover, a method is provided for the preparation of a small amount of a radioactive substance combination. It comprises the following steps:

providing an apparatus adapted for the preparation of a small amount of a chemical substance combination and including a one-part body, a mixing device integrated in the body and adapted to receive a small amount of chemical substances, and at least one receptacle integrated in the body and connected to the mixing device and adapted to hold a small amount of a chemical substance, supplying a small amount of at least one substance into a mixing device of the apparatus, supplying a small amount of at least one radioactive substance into the mixing device, mixing the at least one substance with the at least one radioactive substance, and withdrawing the resulting substance combination.

Small amounts of radioactive substance combinations for an individual dose to be administered to a patient, and in particular biomolecules radiolabelled with isotopes can be prepared by the method of the invention. In contrast to conventional manual methods of preparation, the method according to the invention permits minute quantities of radioactive substance combinations to be prepared so that no excess amounts of substance combinations will be produced which must be disposed of afterwards. The method according to the invention can be carried out with the highest degree of automation, substantially excluding any contamination of persons. Moreover, cleaning and sterilizing measures can be widely dispensed with since the microfluid apparatus utilized in the preparation process preferably is presented in the form of a disposable item and may be dumped after one-time use. As the microfluid apparatus can be manufactured in series the processes of preparing substance combinations are reproducible. Varying the structure of the microfluid apparatus allows different procedures of preparation to be performed. Individualized medicines, however, may be obtained also with an unaltered structure or type of apparatus if different starting substances and different quantities are chosen.

In accordance with an embodiment, the supplying of a small amount of a substance includes supplying an amount of less than 2 ml, preferably less than 1 ml, especially preferred being less than 100 µl. Such tiny quantities are needed, for example, to prepare individual doses of radiolabeled biomolecules.

Preferably, the supplying further includes feeding a substance from a receptacle which is integrated in the apparatus. This receptacle exclusively holds such chemicals needed for the preparation procedure that may be stored over longer periods of time. At least one substance, preferably, is put into the receptacle of the apparatus when the apparatus itself is made. This may be done at the manufacturer's of the apparatus or at a pharmaceuticals supplier's. Once the substance has been filled in, contamination of or by persons getting into contact with the apparatus is substantially excluded.

Moreover, the supply of a radioactive substance preferably is effected from outside the apparatus, for example, from an isotope generator or a suitable container. In this manner the radioactive substance for preparing the radiochemical substance combination and especially for radiolabeling biomolecules can be supplied directly at the place where it will be administered, in other words at the hospital. In addition, the method according to an embodiment may include also cooling or heating of substances.

According to another embodiment, the method includes subjecting one or more substances or substance combinations in the apparatus to quality control. Finally, according to yet another embodiment, also the resulting radiochemical substance combination may be subjected to quality control prior to its withdrawal. Quality control may include performing size exclusion chromatography, ion exchange chromatography, and/or thin film chromatography.

The mixing procedure preferably includes radiolabeling of biomolecules, such as antibodies or peptides with isotopes. As a consequence of the mixing, a chemical bond may be formed between the radioactive substance and the at least one other substance. Preferably, the radioactive substance may be selected from the group including Me2+, Me3+, MeO4−, halogens, cobalt-57, cobalt-58, selenium-75, gallium-67, gallium-68, iodine-123, iodine-124, iodine-125, iodine-131, astatine-211, actinium-225, bismuth-212, bismuth-213, lead-212, technetium-99m, rhenium-186, rhenium-188, silver-111, indium-111, platinum-197, palladium-109, copper-67, phosphorus-32, Phosphorus-33, yttrium-90, scandium-47, samarium-153, ytterbium-169, lutetium-177, rhodium-105, praseodymium-142, praseodymium-143, terbium-161, holmium-166, thallium-201, or gold-199.

Moreover, the method may include supplying a buffer solution selected from the group including acetate and citrate, MES, HEPES, phosphanates, carbonates, and mixtures thereof or any other suitable buffer solution. Finally, the method may include controlling and monitoring the process sequence by means of a control unit adapted to be coupled to the apparatus. In this manner the method of preparation can be largely automated.

An embodiment of the apparatus of the invention will be described, by way of example, with reference to the accompanying drawing.

The FIGURE is a diagrammatic illustration of an apparatus and a microfluid apparatus, respectively, for preparing a small quantity of a radioactive substance combination in cross section.

The apparatus includes a one-part body, if desired, an assembled multi-part body which may be made, for instance, of silicon or plastic. Inside the apparatus, three receptacles 3 are provided, each for holding a respective small amount of a chemical starting substance. The receptacles 3 are integrated in the apparatus and closed towards the outside. They may hold chemical substances which already are filled in, if desired, by a pharmaceuticals producer when the apparatus is made. Depending on the intended use, all the receptacles 3 or only some of them may be filled. The substances filled into the apparatus, preferably, are substances which are suitable for storage and remain substantially unchanged in the course of time. The volume of the receptacles lies in the order of magnitude of a few ml. A conduit 4 is provided substantially in the direction of the longitudinal axis of the apparatus. It may be formed, for example, by etching the silicon body accordingly. The conduit 4 which is shown only diagrammatically in the drawing likewise has a very small volume of a few ml. In its middle portion which accounts for approximately one third of the length of the apparatus, its course is undulated between two straight sections. The middle portion defines a so-called "snake mixer". The apparatus comprises further conduits 5 which connect the receptacles 3 to the central conduit 4. These conduits, too, are formed by etching. In the embodiment illustrated in the FIGURE, the central conduit 4 serves as mixing device for the chemical substances from the receptacles 3. The apparatus further includes connecting members 1 and 2, such as membranes or mechanical locks, disposed at the front and rear ends, respectively, of the central conduit 4. Dissolved isotopes from an upstream isotope source (not shown) may be fed through these connecting members into the microfluid apparatus, and they may be withdrawn from the apparatus through the connecting members.

The microfluid apparatus shown diagrammatically is indicated merely as an example; numerous modifications may be made to this apparatus. For example, accesses (not shown) may be provided through which sensor and measuring means can be inserted among others for quality control. The apparatus, moreover, may comprise dosing and conveying means or parts thereof which are associated with the receptacles and by means of which the chemical substances inside the reservoirs 3 may be fed in predetermined quantities into the central conduit 4. Other than in the embodiment shown, receptacles 3 are conceivable of which the volumes differ. Also the number of conduits and receptacles and their arrangement may differ between various embodiments and may depend on the number of individual substances used to prepare the substance combination. The apparatus, preferably, has small dimensions, for instance, a length of less than 10 cm, a width of less than 5 cm, and a height of less than 2 cm. Yet the dimensions are variable and may be determined, e.g. by the number and sizes of the receptacles, mixing devices, conveying and dosing means etc., in other words by the components integrated in the apparatus.

For automatically controlled preparation and quality monitoring, the apparatus further may include conveying and dosing means, respectively, measuring or sensor means, means for carrying out chromatography or electrophoresis, etc. or parts thereof, and means for receiving control and/or power supply signals for these means.

The apparatus preferably is coupled to a corresponding control unit (not shown) which, for instance, contains a programmable processor or software. That permits substantially automatic preparation of chemical substance combinations.

A finished chemical substance combination, such as biomolecules which are radiolabeled with isotopes may be removed through a connecting member 2.

The apparatus according to the invention may be used in a radiochemical production system for pharmaceutical products for cancer therapy or diagnosis. In that event the apparatus includes, for example, reservoirs filled with the starting substances required for the preparation of a corresponding drug, such as buffer solutions, radical catchers, monoclonal antibodies, etc.

For example, monoclonal antibodies and other biomolecules may be radiolabeled by means of the apparatus and method according to the invention.

Radiolabeling of biomolecules with metal isotopes (Me2+ and Me3+) requires adding functional groups to biomolecules, for example, chelates such as EDTA-, DTPA-, DOTA derivates, and other chelates. It is the task of the functional group to establish a sufficiently stable bond with the metal ions. Some biomolecules themselves represent chelates, for example phosphanate compounds. During the past years also peptides were developed which likewise comprise a metal ion binding part in their molecular structure.

The Me2+ and Me3+ radio isotopes typically are provided in diluted HCl or HNO3 acid solutions. The required quantity of radioactive isotopes is introduced into a buffer solution (typically acetate or citrate) to regulate the pH and bring it into a range which, on the one hand, is suitable for binding of the metal ions to the chelates and, on the other hand, excludes damaging the biomolecules.

The necessary biomolecule quantity is added to the buffered solution, whereupon the mixing process and reaction, respectively, begin. The reaction time depends on the type of the chelate and on the radioactive metal. Some processes require an elevated temperature. After the reaction time, the biomolecules are purified by way of size exclusion or ion exchange chromatography or another suitable procedure to separate them from unbound radioactive metal ions. In some cases it is possible to formulate the radiolabeled biomolecules directly as a radiopharmaceutical substance with sufficient amounts of buffer, without the need for a purification step. Subsequently, quality control of the radiopharmaceutical substances may be performed by resorting to suitable methods, such as size exclusion chromatography, ion exchange chromatography, thin film chromatography, etc.

Another exemplary process includes radiolabeling of biomolecules with (metal)O4− isotopes. In nuclear medicine often TcO4− is used. Interest in the chemical analogue ReO4− for therapeutical applications is growing. Both isotopes usually are kept in saline solution. For radiolabeling biomolecules with MeO4− isotopes it is necessary, first of all, to reduce the MeO4− isotope to a lower oxidation state (Me (IV)) or (Me(V)), accomplished typically by using Sn2+ ions as the reducing agent. The principle of the radiolabeling procedure is substantially the same as described above for radiolabeling biomolecules with Me2+ and Me3+ isotopes. Although both technitium and rhenium ions form complexes with EDTA-, DTPA-, DOTA derivatives it is customary to use specifically designed chelates together with larger biomolecules for these metals.

Another exemplary process to be carried out, using the apparatus according to the invention and the method according to the invention, is radiolabeling of biomolecules with halogens, like iodine or astatine. This may be subdivided essentially into two methods. According to one method, proteins are radiolabeled by halogenation of a tyrosine group in the protein structure, provided the biomolecule includes a tyrosine ring (phenol) or a similar structure. An oxidizing agent, such as chloramine-T or iodogene is used for the reaction. In general, this method is similar to that of radiolabeling biomolecules with Me2+ and Me3+ isotopes, yet an oxidizing agent is provided in the reaction solution. As a result, however, covalent bonds are formed between iodine and carbon in the tyrosine ring, in contrast to the labeling with Me2+ and Me3+ isotopes. Moreover, a purification step generally is required. In another method of radiolabeling biomolecules with halogens, it is possible to halogenate biomolecules by attaching a trialkyl tin group, such as a trimethyl tin or tributyl tin group to the biomolecule. These groups may then be substituted under oxidation conditions by a halogen.

When an examplary mixing procedure or preparation process is to be carried out, appropriately trained persons will take the apparatus out of its protective sheathing and connect it to a control unit. Furthermore, the sterile connectors will be exposed, e.g. by removing a film, and fluid connections will be established with an isotope reservoir and a recipient for the finished product. Furthermore, the type of apparatus and its readiness for operation will be checked and made sure. If necessary, electrical components integrated in the microfluid apparatus may be supplied with current by means of the control unit through terminals provided at the microfluid apparatus. Control of the components provided inside the microfluid apparatus is effected by the control unit connected to the apparatus.

When the production process is started by means of the control unit the individual substances are metered in the right proportions, according to the individualized patient therapy plan, by the conveying and dosing means, respectively, (pumps) which are integrated in or provided at the apparatus, and they are mixed by the mixing device. In a first reservoir 3 of the apparatus, for instance, there is an acetate buffer (0.2 M), while another reservoir holds a quantity of an antibody substance. If desired, a quantity of a chelate forming substance may be provided in another reservoir. A dosing means controlled by the control unit connected to the apparatus transports a desired quantity of the acetate buffer into the mixing device and the central conduit 4, respectively. Furthermore, for example, an yttrium-90 solution (e.g. 100 mCi/ml in 0.04 M HCl) is passed from an isotope source through the connecting member 1 into the mixing device. Thereupon the pH of the substance mixture in the mixing device is determined by a suitable measuring sensor. If the pH should be below 5 more acetate buffer will be introduced into the mixing device under control of the control unit and by means of a dosing device associated with the respective reservoir. If desired, another pH measurement is performed. Finally, a required quantity of the antibody substance is supplied from the reservoir into the mixing device. Thereafter the reaction mixture rests for a sufficient length of time. In addition, the reaction mixture may be purified by means of a size exclusion chromatography device which may be integrated in or external of the apparatus. When a respective reaction time has lapsed various quality control examinations will be undertaken. Finally, radiopharmaceutical conditioning (volume, buffering, isotonic) may take place.

After the mixing and reaction process, respectively, the medicine obtained is transferred into a transportation container and brought to the location of therapy.

Upon administration of the medicine made, the apparatus finally is put into a decay vessel, and when the radioactivity has decayed the apparatus may be disassembled, if desired. The components destined for single use will be disposed of, and any multiple use components will have to undergo cleaning. When new sterile disposable components have been inserted, the cassette will be ready again to be filled and may be used once more for preparing a substance combination. The filling may be done at a pharmaceutical or biotechnology company and preferably under sterile conditions and in accordance with cGMP so that the necessary quality of the substances can be assured.

The features disclosed in the specification and claims may be significant to the invention, both individually and in any combination.

The invention claimed is:

1. An apparatus for preparing a small amount of a radioactive substance combination, comprising:
    a one-part body,
    a mixing device integrated in the body and adapted to receive a small amount of chemical substances, and
    at least one receptacle integrated in the body and connected to the mixing device and adapted to hold a small amount of a chemical substance.

2. The apparatus as claimed in claim 1, wherein one or more of the at least one receptacle has a volume of less than 100 μl.

3. The apparatus as claimed in claim 1, further comprising: one or more conduits integrated in the apparatus and having a volume of less than 100 μl.

4. The apparatus as claimed in claim 3, wherein each conduit has a height of less than 100 μm and a width of less than 500 μm.

5. The apparatus as claimed in claim 2, wherein the mixing device and each of the at least one receptacle are interconnected by a corresponding at least one conduit.

6. The apparatus as claimed in claim 1, wherein the mixing device is a conduit.

7. The apparatus as claimed in claim 1, wherein the mixing device is selected from the group including cascade mixers, diffusion mixers, lamination mixers, mixers operating according to the split-recombine principle, mixers operating with the assistance of alternating electrical fields or with sonic or vibratory support.

8. The apparatus as claimed in claim 5, wherein the mixing device has a holding capacity of less than 100 μl.

9. The apparatus as claimed in claim 1, wherein the apparatus is adapted to be closed and sealed towards the outside.

10. The apparatus as claimed in claim 1, further comprising: at least one access for a sensor, and/or one mechanical interface with the outside.

11. The apparatus as claimed in claim 1, further comprising:
    at least one conveying and dosing means, respectively, selected from the group including: means or a part of means operating with the use of centrifugal force, electrical force acting on a fluid, pressure or volume variation, or a conveying method functioning with sonic or vibratory support.

12. The apparatus as claimed in claim 1, further comprising:
    at least one measuring or sensor means for determining a physical magnitude from among the group including: the type and power of radioactive radiation, pH, and temperature; a means for carrying out chromatography or electrophoresis; and/or a means for detecting refraction of light and/or detecting at least one property of a substance from among the group including the presence or absence, quantity, color, and index of refractivity, an ion exchange column, a size exclusion column or part thereof.

13. The apparatus as claimed in claim 1, wherein the apparatus is controllable from outside and further comprises means for receiving control and/or power supply signals.

14. The apparatus as claimed in claim 1, wherein at least parts of the apparatus are manufactured as a monolith via micro process engineering, including micro injection molding or micro embossing.

15. The apparatus as claimed in claim 1, wherein, at the inside, the apparatus comprises coated surfaces to prevent substances from adhering or for catalyzing chemical reactions.

16. The apparatus as claimed in claim 1, further comprising: a heating and/or cooling device or part thereof 17. The apparatus as claimed in claim 1, wherein the apparatus is made of plastics, polyethylene, polypropylene, polymethylmethacrylate, cyclo-olefin-copolymer (COC), polytetrafluoroethylene, polycarbonate, silicon, metal, or glass.

18. A system, comprising:
an apparatus for preparing a small amount of a radioactive substance combination, wherein the apparatus comprises:
a one-part body;
a mixing device integrated in the body and adapted to receive a small amount of chemical substances; and
at least one receptacle integrated in the body and connected to the mixing device and adapted to hold a small amount of a chemical substance; and
a control unit adapted to be coupled to the apparatus for control thereof.

19. The system as claimed in claim 18, further comprising:
an isotope source adapted to be coupled to the apparatus, and
another source of chemical substances not integrated in the apparatus.

20. The system as claimed in claim 18, further comprising:
a conveying and dosing means, respectively, adapted to be coupled to the apparatus;
measuring or sensor means;
a means for carrying out chromatography or electrophoresis; and/or
a means for detecting refraction of light and/or detecting at least one property of a substance from among the group including the presence or absence, quantity, color, and index of refractivity, an ion exchange column, a size exclusion column or part thereof.

21. A method of preparing a small amount of a radioactive substance combination comprising:
providing an apparatus adapted for preparing a small amount of a chemical substance combination, wherein the apparatus comprises:
a one-part body,
a mixing device integrated in the body and adapted to receive a small amount of chemical substances, and
at least one receptacle integrated in the body and connected to the mixing device and adapted to hold a small amount of a chemical substance;
supplying a small amount of at least one substance into the mixing device of the apparatus;
supplying a small amount of at least one radioactive substance into the mixing device;
mixing the at least one substance with the at least one radioactive substance; and
withdrawing the resulting substance combination.

22. The method as claimed in claim 21, wherein supplying of a small amount of the at least one substance comprises supplying an amount of less than 1 ml.

23. The method as claimed in claim 21, further comprising: supplying a substance from a receptacle which is integrated in the apparatus.

24. The method as claimed in claim 21, wherein at least one substance is introduced into a receptacle of the apparatus when the apparatus is manufactured.

25. The method as claimed in claim 21, wherein supplying a small amount of at least one radioactive substance comprises supplying the radioactive substance from outside the apparatus.

26. The method as claimed in claim 21, further comprising: cooling or heating of substances.

27. The method as claimed in claim 21, further comprising: performing quality control of one or more substances or substance combinations in the apparatus.

28. The method as claimed in claim 21, further comprising: performing quality control of the resulting radiochemical substance combination prior to withdrawal.

29. The method as claimed in claim 21, wherein performing quality control comprises performing size exclusion chromatography, ion exchange chromatography, and/or thin film chromatography.

30. The method as claimed in claim 21, wherein mixing the at least one substance with the at least one radioactive substance comprises radioactive labeling of biomolecules with isotopes.

31. The method as claimed in claim 21, wherein mixing the at least one substance with the at least one radioactive substance results in a chemical bond between the at least one radioactive substance and the at least one substance.

32. The method as claimed in claim 21, wherein the at least one radioactive substance is selected from the group including Me2+, Me3+, MeO4−, and halogens.

33. The method as claimed in claim 21, wherein the at least one radioactive substance is selected from the following group: cobalt-57, cobalt-58, selenium-75, gallium-67, gallium-68, iodine-123, iodine-124, iodine-125, iodine-131, astatine-211, actinium-225, bismuth-212, bismuth-213, lead-212, technetium-99m, rhenium-186, rhenium-188, silver-111, indium-111, platinum-197, palladium-109, copper-67, phosphorus-32, phosphorus-33, yttrium-90, scandium-47, samarium-153, ytterbium-169, lutetium-177, rhodium-105, praseodymium-142, praseodymium-143, terbium-161, holmium-166, thallium-201, or gold-199.

34. The method as claimed in claim 21, further comprising: supplying a buffer solution selected from the group including acetate, citrate, phosphanate, carbonate, HEPES, MES, or other acceptable buffer solutions.

35. The method as claimed in claim 21, further comprising: controlling and monitoring the method sequence by means of a control unit adapted to be coupled to the apparatus.

* * * * *

UNITED STATES PATENT AND TRADEMARK OFFICE
CERTIFICATE OF CORRECTION

| | | |
|---|---|---|
| PATENT NO. | : 7,605,384 B2 | Page 1 of 1 |
| APPLICATION NO. | : 11/816152 | |
| DATED | : October 20, 2009 | |
| INVENTOR(S) | : Julian Bernd Sonnenhol et al. | |

It is certified that error appears in the above-identified patent and that said Letters Patent is hereby corrected as shown below:

Column 3,
Line 29, "first place serve" should read --first place, serve--.

Signed and Sealed this
First Day of March, 2011

David J. Kappos
*Director of the United States Patent and Trademark Office*